United States Patent
Szabo et al.

(10) Patent No.: US 8,267,942 B2
(45) Date of Patent: Sep. 18, 2012

(54) SYSTEMS AND METHODS FOR CLOSING A VESSEL WOUND

(75) Inventors: David Szabo, Doylestown, PA (US); David Gale, Cambridge (GB); Paul Johnson, Cherry Hinton (GB); Valerie Scott, Cambridge (GB); Ben Morris, Louisville, KY (US); Greg Furnish, Louisville, KY (US); Trevor Beckett, Milton (GB); Michael J. Trezza, II, Pittstown, NJ (US)

(73) Assignees: Ethicon, Inc.; Cordis Corporation

( * ) Notice: Subject to any disclaimer, the term of this patent is extended or adjusted under 35 U.S.C. 154(b) by 970 days.

(21) Appl. No.: 11/317,478

(22) Filed: Dec. 23, 2005

(65) Prior Publication Data

US 2007/0150002 A1    Jun. 28, 2007

(51) Int. Cl.
*A61B 17/04* (2006.01)

(52) U.S. Cl. ........ 606/139; 606/142; 606/144; 606/148; 606/232

(58) Field of Classification Search .................. 606/213, 606/139–158, 191
See application file for complete search history.

(56) References Cited

U.S. PATENT DOCUMENTS

| | | | | |
|---|---|---|---|---|
| 4,235,238 A | * | 11/1980 | Ogiu et al. ..................... | 606/145 |
| 5,021,059 A | | 6/1991 | Kensey et al. | |
| 5,085,661 A | * | 2/1992 | Moss ............................ | 606/139 |
| 5,282,827 A | | 2/1994 | Kensey et al. | |
| 5,324,306 A | | 6/1994 | Makower et al. | |
| 5,354,271 A | | 10/1994 | Voda | |
| 5,383,896 A | | 1/1995 | Gershony et al. | |
| 5,391,183 A | | 2/1995 | Janzen et al. | |
| 5,441,517 A | | 8/1995 | Kensey et al. | |
| 5,545,178 A | * | 8/1996 | Kensey et al. ................ | 606/213 |
| 5,645,566 A | | 7/1997 | Brenneman et al. | |
| 5,662,681 A | | 9/1997 | Nash et al. | |
| 5,665,107 A | | 9/1997 | Hammerslag | |
| 5,690,674 A | | 11/1997 | Diaz | |

(Continued)

FOREIGN PATENT DOCUMENTS

WO    98/11830 A1    3/1998

(Continued)

OTHER PUBLICATIONS

European Search Report dated Oct. 7, 2009 relating to corresponding European Application No. 09075397.1.

(Continued)

*Primary Examiner* — Corrine M McDermott
*Assistant Examiner* — Mark Mashack

(57) ABSTRACT

Vessel wound closure systems and method for sealing a puncture wound in a target vessel, such as those puncture wounds that occur from prior interventional procedures. A sealing member is deployed intravascularly into the target vessel, and an anchor member is deployed extravascularly of the target vessel. The sealing member and the anchor member are connected by a suture that may be drawn to tighten the sealing member and the anchor member relative to one another in order to effect the seal of the puncture wound. After tightening, the suture is secured to maintain the sealing member and the anchor member relative to one another in order to maintain the seal. Preferably, the anchor member, the suture and the sealing member are comprised of biocompatible, bioresorbable materials that are absorbed into the body after the sealing of the puncture wound has been achieved. The sealing member, suture and the anchor member are delivered by a delivery rod or other components over a guidewire or through an introducer already in place from the preceding interventional procedure.

11 Claims, 9 Drawing Sheets

U.S. PATENT DOCUMENTS

| | | | |
|---|---|---|---|
| 5,741,223 A | 4/1998 | Janzen et al. | |
| 5,792,152 A | 8/1998 | Klein et al. | |
| 5,810,884 A * | 9/1998 | Kim | 606/213 |
| 5,868,778 A | 2/1999 | Gershony et al. | |
| 6,383,199 B2 * | 5/2002 | Carter et al. | 606/148 |
| 6,554,852 B1 * | 4/2003 | Oberlander | 606/232 |
| 6,626,919 B1 * | 9/2003 | Swanstrom | 606/153 |
| 7,056,325 B1 * | 6/2006 | Makower et al. | 606/153 |
| 7,087,064 B1 * | 8/2006 | Hyde | 606/142 |
| 7,740,638 B2 * | 6/2010 | Hyde | 606/139 |
| 2001/0039426 A1 * | 11/2001 | Makower et al. | 606/153 |
| 2003/0144695 A1 | 7/2003 | McGuckin et al. | |
| 2004/0006352 A1 | 1/2004 | Nobles et al. | |
| 2004/0162568 A1 * | 8/2004 | Saadat et al. | 606/139 |

FOREIGN PATENT DOCUMENTS

| | | |
|---|---|---|
| WO | WO 98/52472 A | 11/1998 |
| WO | 2005/063133 A1 | 7/2005 |

OTHER PUBLICATIONS

European Office Action dated Apr. 2, 2009 relating to corresponding European Application No. 06 845 394.3.

Examiner's first report for Australian Patent Application No. 2006333048 dated Nov. 16, 2011.

English language translation of Notification of Reasons for Refusal dated Jan. 10, 2012 for Japanese Patent Application No. 2008-547326.

* cited by examiner

SYSTEMS AND METHODS FOR CLOSING A VESSEL WOUND

BACKGROUND OF TH INVENTION

1. Field of the Invention

The invention generally relates to vessel wound closure techniques. More particularly, the invention relates to systems and methods for sealing puncture wounds in a blood vessel such as those that result from certain interventional procedures.

2. Related Art

A large number of therapeutic and diagnostic procedures involve the percutaneous introduction of instrumentation into a blood vessel, for example, percutaneous transluminal coronary angioplasty (PTCA). Such procedures most often involve accessing an intended site through the femoral artery. Ideally, closing and healing of the resultant vascular puncture wound successfully completes the procedure.

Traditionally, the application of external pressure to the skin at the entry site of the instrumentation into the patient has been employed to stem bleeding from the wound. A nurse or physician, for example, applies pressure to the wound site until clotting and tissue rebuilding has occurred sufficiently to seal the perforation. In some situations, the external pressure is maintained for an hour or more, during which time the patient is uncomfortably immobilized. Thus patient comfort and physician efficiency are impaired where such external pressure techniques are employed.

Additionally, the risk of hematoma exists while bleeding from the vessel occurs. Such hematoma risk continues until sufficient clotting of the wound site occurs. Moreover, external pressure devices, such as femoral compression systems, are often unsuitable for some patients, such as those with substantial amounts of subcutaneous adipose tissue, as the skin surface may be a considerable distance away from the vasculature puncture site. Inaccurate skin compression, and thus less effective wound healing, tends to occur as a result.

U.S. Pat. No. 5,383,896 to Gershony, et al. discloses a device that applies pressure to a puncture site internally for a limited period of time, after which the device is removed. The device in Gershony includes a shaft with an expandable balloon and a guidewire tip at its distal end. The distal end of the device is introduced into a blood vessel through an introducer sheath that is typically used in percutaneous interventional procedures. The balloon is then inflated and withdrawn until the balloon hemostatically engages the inner surface of the blood vessel, after which the introducer sheath is removed. A fixation collar on the shaft applies tension to the balloon for a medically sufficient time and thereafter the balloon is deflated and the entire device is removed from the body.

U.S. Pat. No. 5,645,566 to Brenneman, et al. discloses a device that applies pressure to the outside wall of a punctured blood vessel from a distance using a balloon, a sheet and a foam pad. The pressure applying device is located using a balloon in the vessel (similar to that of Gershony) and a radiopaque marker.

PCT Application WO 98/11830, published Mar. 26, 1998, S. Barak, Inventor, discloses various embodiments of an apparatus for hemostasis. Among them is a device that positions an anchor against an inner surface of an artery wall and a balloon outside the wall. The balloon is inflated to pinch the artery wall, after which the anchor is withdrawn. The balloon is maintained against the puncture until hemostasis is achieved. The anchor and balloon are removed after hemostasis is achieved.

Other arterial closure devices include bioabsorbable materials intended to remain in the body until they are absorbed as in related U.S. Pat. Nos. 5,282,827 and 5,441,517, which disclose an anchor inserted into a vessel and urged against an inner wall of the vessel as a collagen plug is deployed externally of the puncture site to expand and fill the tissue tract leading to the puncture site. A filament attaches the plug to the anchor and moves the plug and anchor relative to one another in pulley-like fashion to effect a seal at the puncture site. After emplacement, a tamping member may be used to urge the plug against the external puncture site to help seal the same.

U.S. Pat. No. 5,662,681 discloses an arterial closure device in which an anchor and plug are attached to one another via a filament. The anchor is inserted into the vessel and urged against the interior wall of the vessel as the plug is urged against the exterior wall of the vessel at a puncture site. A separate locking means moves the plug and anchor relative to one another to maintain the plug and anchor in sealing position at the puncture site.

U.S. Pat. No. 5,391,183 to Janzen, et al. describes a device that inserts hemostatic material through a tissue channel and against the outside wall of the vessel around the puncture site.

U.S. Pat. No. 5,690,674 to Diaz discloses a biodegradable plug that has two substantially parallel disks joined at their centers by a waist. The plug is positioned so that the distal disk is on the interior wall of the blood vessel, the proximal disk is on the exterior wall, and the waist is in the wound of the vessel wall.

Another known closure device includes U.S. Pat. No. 5,741,223 to Janzen, et al. This '223 patent discloses the placement of a plug to seal a puncture site.

U.S. Pat. No. 5,354,271 to Voda discloses suture threads with barbed ends, wherein the suture threads are deployed into a vessel and then the barbed ends penetrate through the vessel wall and expand to prevent retraction thereof back into the vessel. The suture threads are then tied or otherwise secured across the puncture site.

U.S. Pat. No. 5,324,306 discloses a mass of hemostatic material pushed against the outside wall of a vessel at a puncture site. Manual pressure is applied to ensure blood flow has stopped.

U.S. Pat. No. 5,868,778 discloses a balloon used in combination with a procoagulant injected at the puncture site in order to seal a puncture site of a vessel.

U.S. Pat. No. 5,792,152 discloses a flexible needle with suture attached thereto that is deployed across a puncture site of a vessel. The flexible needle and suture are introduced into the vessel via an entry lumen, proceed through a U-shaped return lumen, and exit the vessel through an exit lumen. Thereafter the suture is drawn further outward from the vessel and tied or otherwise secured across the puncture site.

U.S. Patent Publication No. 2004/0006352 discloses an arterial closure device comprising an assembly in which clasp arms, to which a suture is initially secured, are deployed within a vessel. Penetrating members including suture catches are then separately deployed to snag or capture the sutures associated with a respective clasp arm. The sutures are then pulled taught by pulling the penetrating member with suture catches out from the vessel, and then tied or otherwise secured to close the puncture site. Thereafter the assembly is withdrawn from the body.

SUMMARY OF THE INVENTION

The various embodiments described herein comprise vessel wound closure systems and methods for closing a puncture wound in a target vessel.

In some embodiments the system comprises an outer sheath, a delivery rod slidably disposed within the outer sheath, a guidewire slidably associated with the delivery rod, a sealing member deployably housed within the outer sheath, and a anchor member deployably housed within the delivery rod, and a connecting suture connecting the sealing member and the anchor member, whereby the outer sheath encircles the delivery rod and constrains the sealing member, the connecting suture and the anchor member from deploying until sufficient proximal movement of the outer sheath has occurred. Upon deployment, the sealing member is positioned intravascularly about the inside surface of the target vessel, the anchor member is positioned extravascularly about the outside surface of the target vessel, and the sealing member and the anchor member are moved closer to one another by drawing and securing the connecting suture in order to seal the vessel wound. A portion of the connecting suture extends proximal of the anchor member and is accessible to a medical practitioner beyond a proximal end of the delivery rod and the outer sheath to help tighten the sealing member and the anchor member relative to one another.

The delivery rod further comprises an exterior channel and a tapered distal section through which the guidewire slides for locating the system within the target vessel. The delivery rod further comprises a first recess in which the sealing member is oriented for deployment therefrom, a second recess in which the anchor member is oriented for deployment therefrom, and an open channel between the first recess and the second recess in which open channel the connecting suture extends between the sealing member and the anchor member for deployment therefrom.

The system may further comprise a tamping tool to help push or maintain the anchor member in place as the sealing member and the anchor member are tightened by drawing the connecting suture after deployment. Once sufficiently tightened and secured, a separate cutting element is provided through the delivery rod to cut excess suture material, after which the system is removed from the patient's body.

The sealing member and the anchor member are preferably further comprised of bioresorbable material, wherein the sealing member is generally larger than the anchor member in order to effect the seal of the vessel wound. The connecting suture may further comprise one way barbs associated therewith that help secure the sealing member and the anchor member in place relative to one another after sufficient tightening thereof has occurred to seal the vessel wound.

In practice, the delivery rod is inserted through the outer sheath and over the guidewire into the target vessel through the vessel wound. The sealing member is deployed in the target vessel by partially retracting the outer sheath. The sealing member is positioned against an interior wall of the vessel by partial withdrawal of the entire system until resistance is felt by the medical practitioner. The anchor member and the connecting suture are then deployed by further retraction of the outer sheath. The anchor member is then positioned against the exterior wall of the vessel, and the accessible portion of the connecting suture proximal of the delivery rod and outer sheath is manipulated by the medical practitioner to draw and tighten the sealing member and the anchor member relative to one another on either side of the vessel. Once tightened, the connecting suture is secured to effect the seal about vessel wound by the sealing member and the anchor member. A tamping tool may be used to help push or maintain the anchor member in place as tightening occurs. After tightening and securement has occurred, excess suture material is cut and the system removed from the patient's body.

In other embodiments, the vessel wound closure system comprises an introducer, an outer sheath slidably disposed through the introducer from a proximal first position, to a distal second position at, or beyond, a distal end of the introducer, and to a partially proximally withdrawn third position, an inner sheath slidably disposed through the outer sheath between a proximal first position and a distal second position at, or beyond, a distal end of the outer sheath in the third position, a handle associated with the outer sheath and the inner sheath, a plunger having a support rod associated therewith and extending through the handle and within the inner sheath for controlling disposition of an anchor member and a sealing member, the sealing member configured to deploy from the distal end of the outer sheath when in the third position, the anchor member configured to deploy from the distal end of the inner sheath, and a connecting suture connecting the sealing member and the anchor member. Deployment of the sealing member within the target vessel occurs when the outer sheath is in the third position, whereas deployment of the anchor member occurs by depression of the plunger when the inner sheath is in the second position. The support rod provided within the inner sheath includes a tamper at its distal end for helping to push or maintain the anchor member in place as the anchor and sealing members are being tightened and secured by manipulation of the suture. The support rod may further comprise a recessed portion and a cutting member for cutting excess suture material after tightening and securing of the sealing member and the anchor member has occurred.

The introducer may further comprise a flared end into which a hub of the outer sheath is received when disposing the outer sheath to its distal second position and into the target vessel. The handle may further comprise a removable pull-tab extending from the handle and precluding the inner sheath from movement to its distal second position until removal of the pull-tab has occurred. The distal end of the inner sheath may further comprise an angled exit port that helps orient the sealing member or anchor member to effect the sealing of the vessel wound upon deployment thereof.

A portion of the suture extends proximal of the anchor member and is accessible to a medical practitioner to help tighten the sealing member and the anchor member relative to one another after deployment thereof. Thereafter, the suture is secured to maintain the sealing member and the anchor member in position about the vessel wound, excess suture material is cut by a cutter provided within the inner sheath, and the unsecured components of the system are removed from the patient.

In practice, the outer sheath is inserted through the introducer and partially withdrawn to the third position in order to deploy the sealing member in the target vessel. The handle is then moved distally to locate the inner sheath at its second position at, or beyond, the distal end of the outer sheath, which helps ensure that the anchor member is successfully deployed in the target vessel. Thereafter, the assembly of the outer sheath, inner sheath, handle, plunger, and support rod is partially withdrawn until resistance is felt by the medical practitioner indicating the sealing member is oriented against an interior surface of the target vessel. The plunger is then depressed to expel the anchor member therefrom the inner sheath and to dispose the anchor member extravascularly along the outer surface of the target vessel. Thereafter, the accessible portion of the suture is manipulated by the medical practitioner to tighten and secure the sealing member and the anchor member relative to one another to effect the seal of the vessel wound. Excess suture material is then cut and unsecured portions of the system are removed from the patient.

The above and other features of the invention, including various novel details of construction and combinations of parts, will now be more particularly described with reference to the accompanying drawings and claims. It will be understood that the various exemplary embodiments of the invention described herein are shown by way of illustration only and not as a limitation thereof. The principles and features of this invention may be employed in various alternative embodiments without departing from the scope of the invention.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE INVENTION

Figure 1:
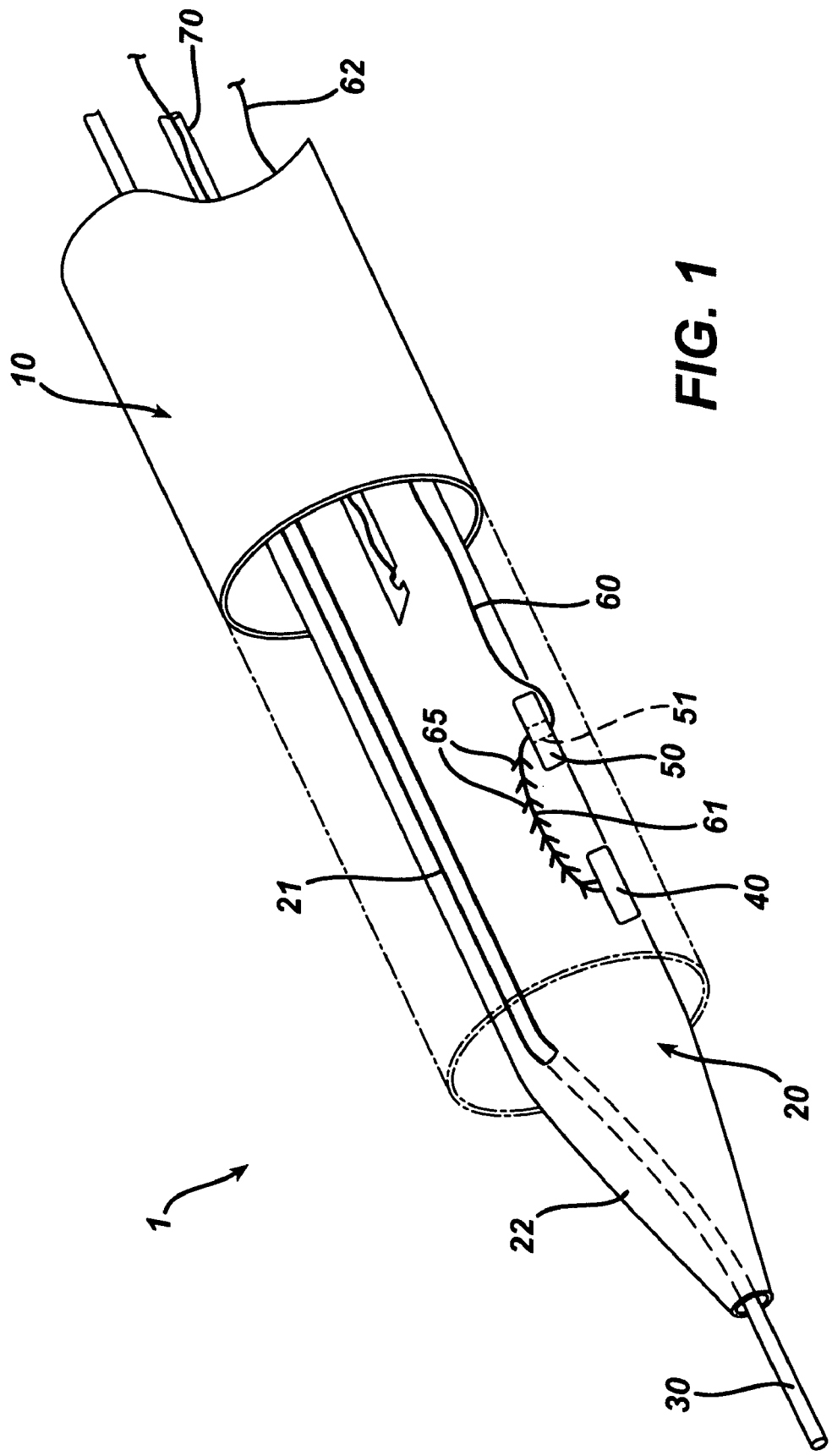
FIG. 1 schematically illustrates an embodiment of a vessel wound closure system according to the description herein.

FIG. 1 illustrates one embodiment of a vessel wound closure system, wherein the term proximal, or variants thereof, is understood as closest to a medical practitioner operator, and the term distal, or variants thereof, is understood as furthest from a medical practitioner operator.

As shown in FIG. 1, the system comprises an outer sheath 10, a delivery rod 20 slidably disposed within the outer sheath 10, a guidewire 30 slidably associated with the delivery rod 20, a sealing member 40 deployably housed within the delivery rod 20, a anchor member 50 deployably housed within the delivery rod 20, and a suture 60 having a connecting portion 61 connecting the sealing member and the anchor member and an accessible portion 62 extending beyond a proximal end of the delivery rod 20 and the outer sheath 10, whereby the outer sheath 10 and the delivery rod 20 are configured such that at a first position the outer sheath 10 prevents the sealing member 40, the suture 60, and the anchor member 50 from deploying (dashed lines), and at a second position, when the outer sheath 10 and delivery rod 20 have been moved relative to one another, the sealing member 40, the suture 60 and the anchor member 50 are deployable. Upon deployment, the sealing member 40 is positioned intravascularly about an inside surface of a target vessel V, the anchor member 50 is positioned extravascularly about an outside surface of the target vessel V, and the sealing member 40 and the anchor member 50 are moved closer to one another by drawing and securing the connecting suture 60 in order to seal the vessel wound. The accessible portion 62 of the connecting suture 60 extends proximal of the anchor member 50 and beyond a proximal end of the delivery rod and the outer sheath for the medical practitioner to manipulate to help tighten the sealing member 40 and the anchor member 50 relative to one another.

Figure 2:
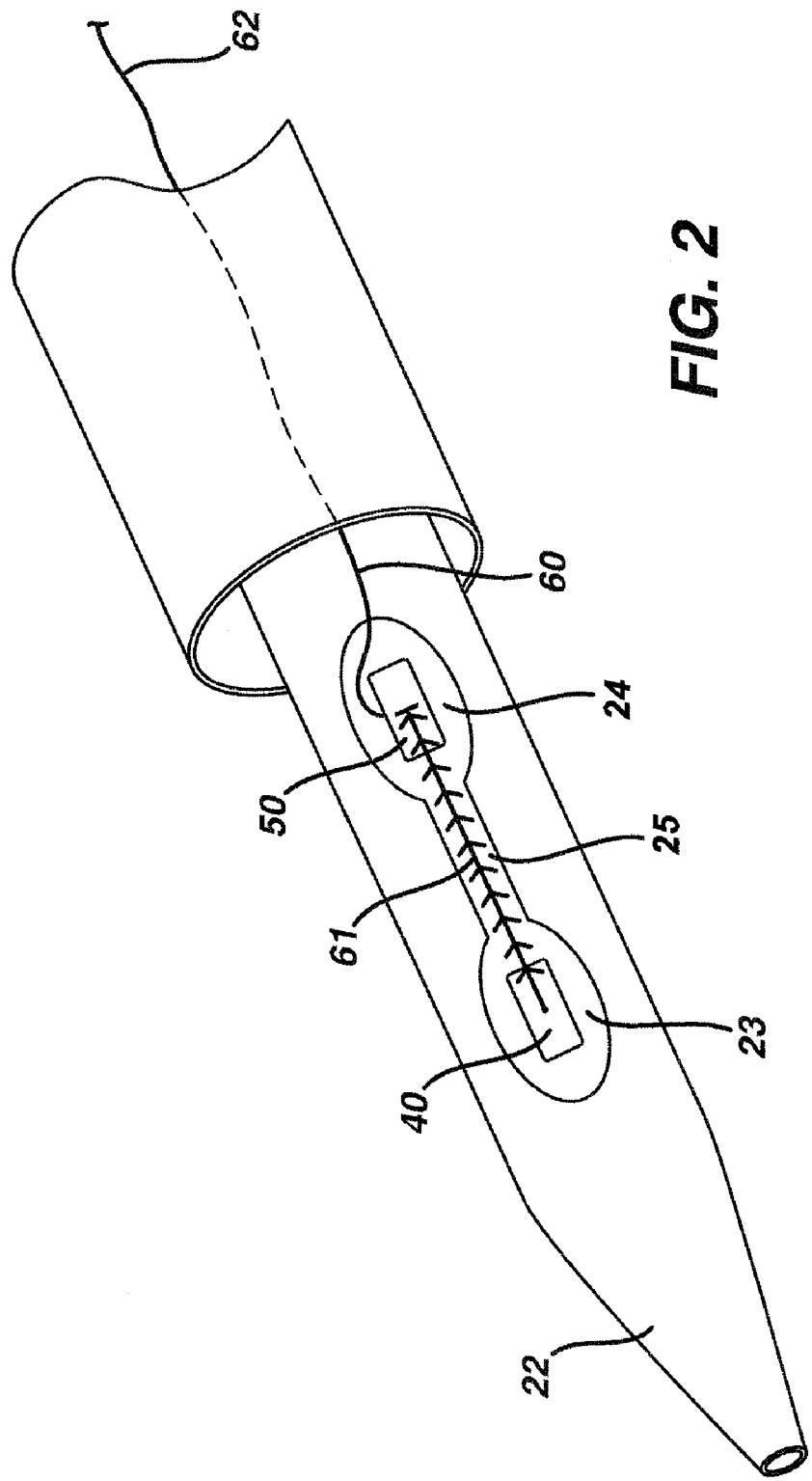
FIG. 2 schematically illustrates a partial view of an embodiment of a delivery rod having a first recess, a second recess, and an open channel therebetween according to the description herein.

Referring to FIGS. 1 and 2, the delivery rod 20 further comprises an exterior channel 21 and a tapered distal section 22 through which the guidewire 30 slides for locating the system 1 within the target vessel V. The delivery rod 20 further comprises a first recess 23 in which the sealing member 40 is oriented for deployment therefrom, a second recess 24 in which the anchor member 50 is oriented for deployment therefrom, and an open channel 25 between the first recess 23 and the second recess 24 and in which open channel 25 the connecting portion 61 of the suture 60 extends for deployment therefrom.

Figure 3A:
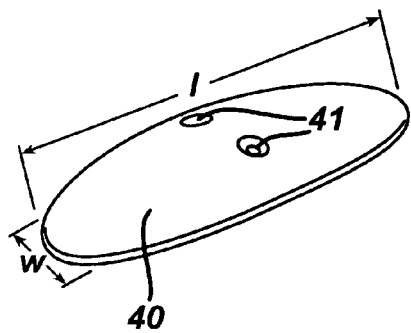
FIGS. 3A-3F illustrate various designs and shapes of the distal or anchor member according to the description herein.
Figure 3B:
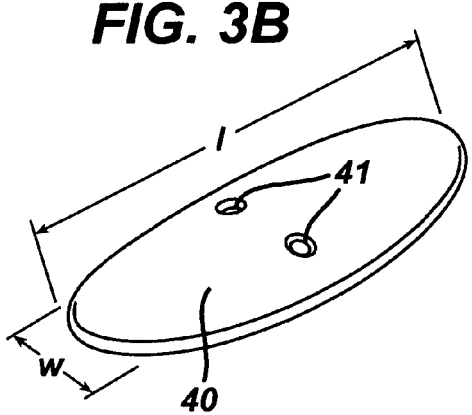

The system 1 may further comprise a tamping tool 80 (FIG. 3G), at least a portion of which is disposed within the delivery rod 20, to help push or maintain the anchor member 50 in place as the sealing member 40 and the anchor member 50 are tightened by drawing the connecting suture 60 after deployment. Once sufficiently tightened and secured, a separate cutting element 70 (FIG. 1), at least a portion of which is provided through the delivery rod 20, may be used to cut excess suture material, afterwhich the various unsecured components of the system 1 are removed from the patient's body.

The sealing member 40 and the anchor member 50 are preferably further comprised of bioresorbable material, wherein the sealing member 40 is generally larger than the anchor member 50 in order to effect the seal of the vessel wound. The connecting portion 61 of the suture 60 may further comprise one way barbs 65, or other self-locking elements, associated therewith that help secure the sealing member 40 and the anchor member 50 in place relative to one another after sufficient tightening thereof has occurred to seal the vessel wound. In the case of one way barbs 65, the anchor member 50 is further comprised of at least one passageway 51 through which the barbs 65 may proceed as the suture 60 is drawn to tighten and secure the sealing member 40 and the anchor member 50 relative to one another to effect the seal of the vessel wound.

Figure 3C:
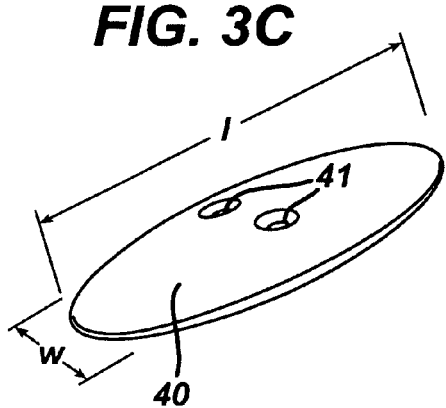
Figure 3D:
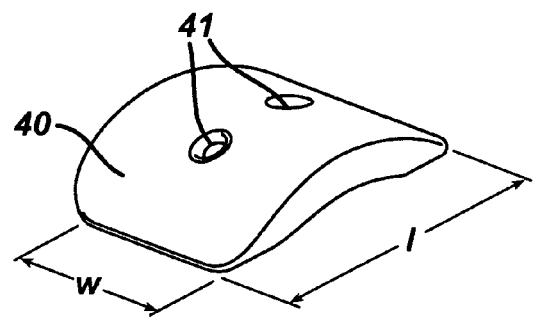
Figure 3E:
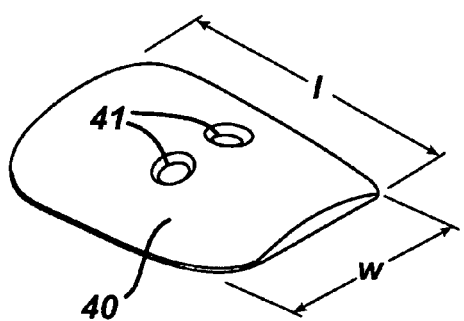
Figure 3F:
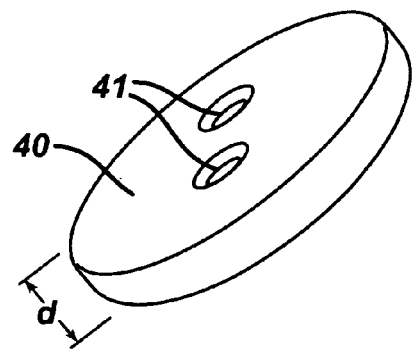

FIGS. 3A-3F illustrate various designs and shapes of the sealing member 40 wherein the elliptical shape of FIG. 3C and the cylindrical shape of FIG. 3D are the preferred designs or shapes for intravascular sealing of the vessel wound. Ideally, a width (w) or diameter (d) of the sealing member 40 is less than the inner diameter of the delivery rod 20 or outer sheath 10 from which the sealing member 40 is deployed. Ideally also, the length (l) or diameter (d) of the sealing member 40 is sufficient to create a good seal against the interior vessel wall while minimizing undesirable positioning of the sealing member 40 during deployment thereof. A length (l) of 10.2 mm and a width (w) of 2.65 mm is preferred when using an 8 Fr sheath having an inner diameter of 2.7 mm, for example. The anchor member 50 may be comprised of similar designs and shapes, although the anchor member 50 is generally smaller than the sealing member 40. The materials comprising the sealing member 40 and the anchor member 50 are bioabsorbable and biocompatible materials that ideally resorbs or endothelializes to minimize the chance of embolism in the target vessel V.

The various designs and shapes of the sealing member 40 shown in FIGS. 3A-3F further comprise at least one passageway 41 through which the suture 60 is threaded. The anchor member 50 further comprises at least one passageway 51 (FIG. 1) similar to the at least one passageway 41 of the sealing member 40. The connecting portion 61 of the suture 60 thus threads through the respective at passageways 41, 51 of the sealing member and the anchor member 50 in order to connect the feet and to enable the drawing and tightening thereof. Alternatively, a distal end of the connecting portion 61 of the suture 60 may be attached to the sealing member 40, as shown in FIGS. 1 and 2, for example, and threaded through the at least one passageway 51 provided in the anchor member 50 in order to connect the sealing member 40 and the anchor member 50 and to enable the drawing and tightening thereof.

Figure 4A:
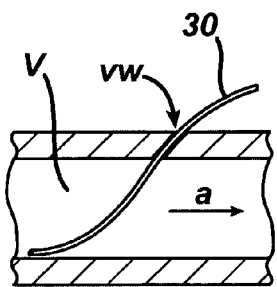
FIGS. 4A-4G illustrate steps for deploying the vessel wound closure system of FIG. 1 according to the description herein.
Figure 4B:
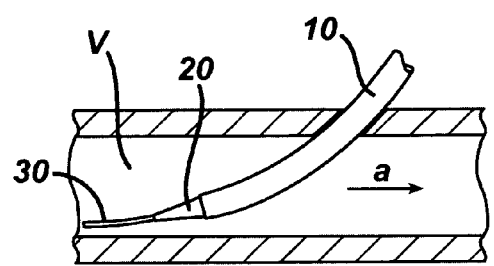
Figure 4C:
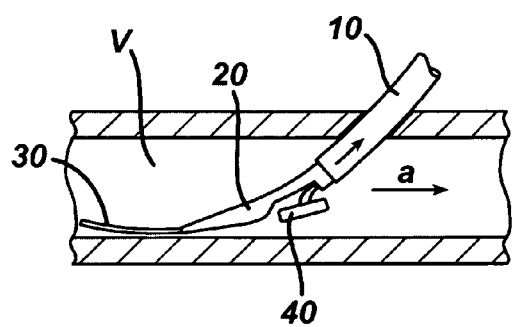
Figure 4D:
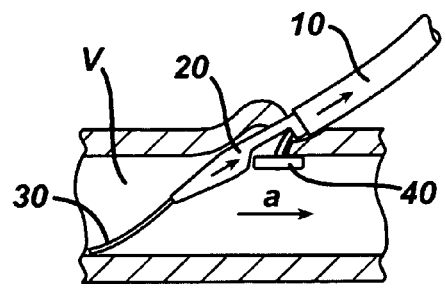
Figure 4E:
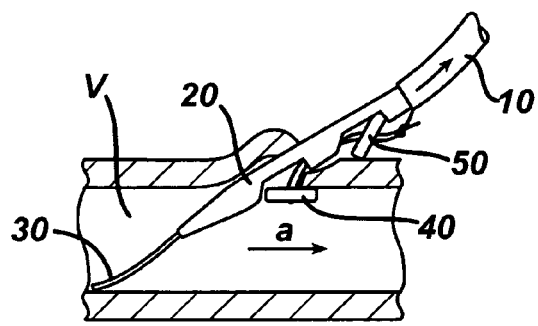
Figure 4F:
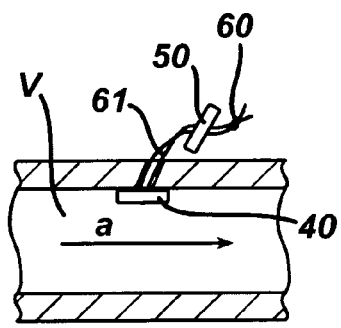
Figure 4G:
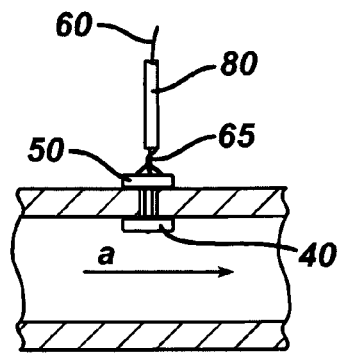

In practice, referring to FIGS. 4A-4G, deployment of the vessel wound closure system and sealing of a vessel wound (vw) is described. In particular, in FIG. 4A the guidewire 30 is in place through the vessel wound, as from a preceding procedure, and into the target vessel V. Blood flow within the target vessel is shown by arrow a. In FIG. 4B, the delivery rod 20, having the sealing member and the anchor member connected by the suture loaded therein, is inserted through the outer sheath 10 and over the guidewire 30 into the target vessel V through the vessel wound. In FIG. 4C, the sealing member 40 is deployed in the target vessel by partially retracting the outer sheath 10. In FIG. 4D, the sealing member 40 is then positioned against an interior wall of the vessel by partial withdrawal of the deployment rod 20 and outer sheath 10 until resistance is felt by the medical practitioner indicating the sealing member 40 has oriented against the interior vessel wall. In FIG. 4E, the anchor member 50 and the connecting portion 61 of the suture 60 are then deployed outside the vessel and through the vessel wound, respectively, by further retraction of the outer sheath 10. In FIG. 4F, the anchor member 50 is then positioned against the exterior wall of the vessel, and the accessible portion 62 of the suture 60 proximal of the delivery rod 20 and outer sheath 10 is manipulated by the medical practitioner to draw and tighten the sealing member 40 and the anchor member 50 relative to one another on either side of the vessel in order to effect the seal of the vessel wound. Once tightened, the suture 60 is secured, by one way barbs 65 or other self-locking elements, to maintain the seal of vessel wound by the sealing member 40 and the anchor member 50. In FIG. 4G, a tamping tool 80 is illustrated that may be used to help push or maintain the anchor member 50 in place as tightening and securement occurs. Such tamping would occur after deployment of the anchor member 50 has occurred, as in FIG. 4E, for example. After tightening and securement of the sealing member, the anchor member and the suture has occurred, excess suture material is cut and unsecured portions of the system are removed from the patient's body.

Figure 5:
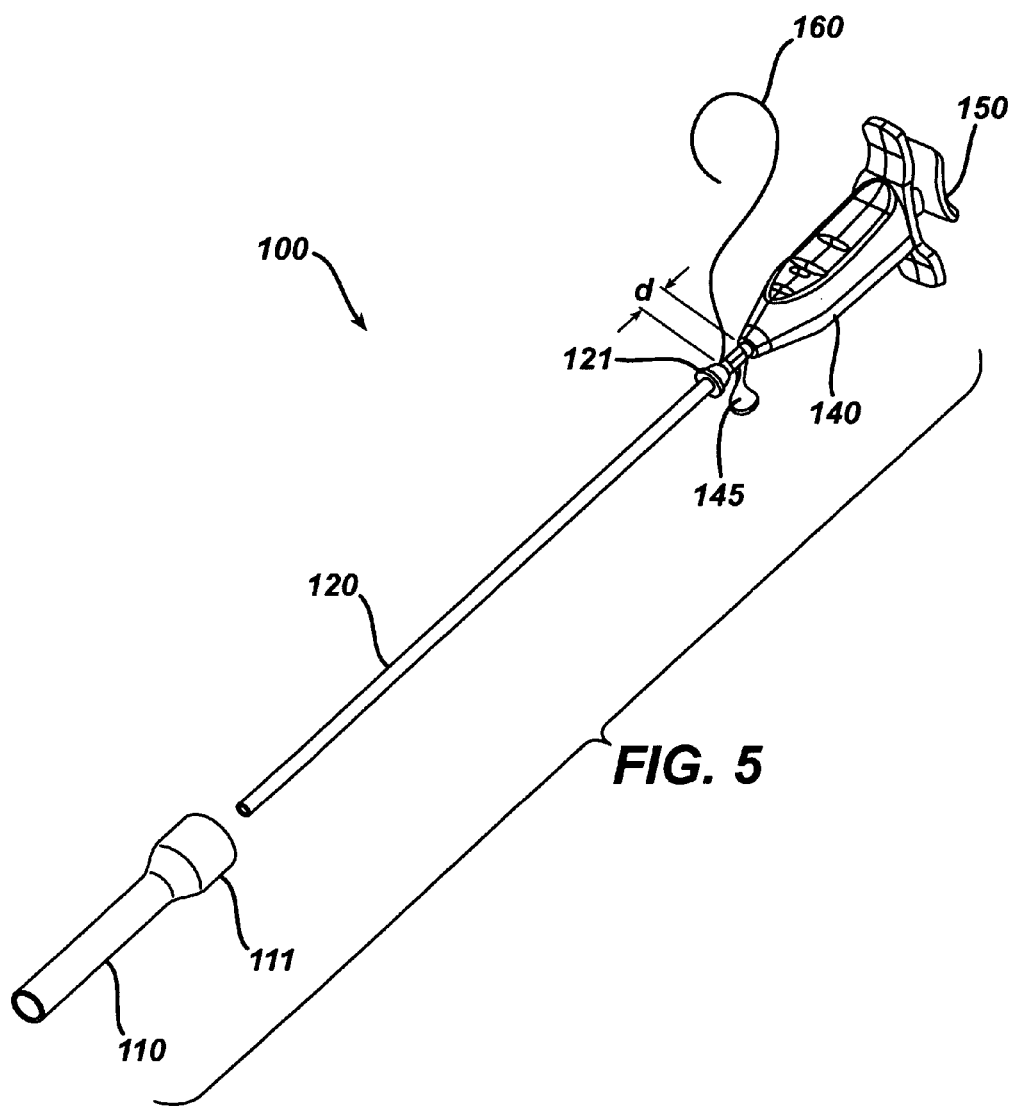
FIG. 5 illustrates another embodiment of a vessel wound closure system according to the description herein.
Figure 6:
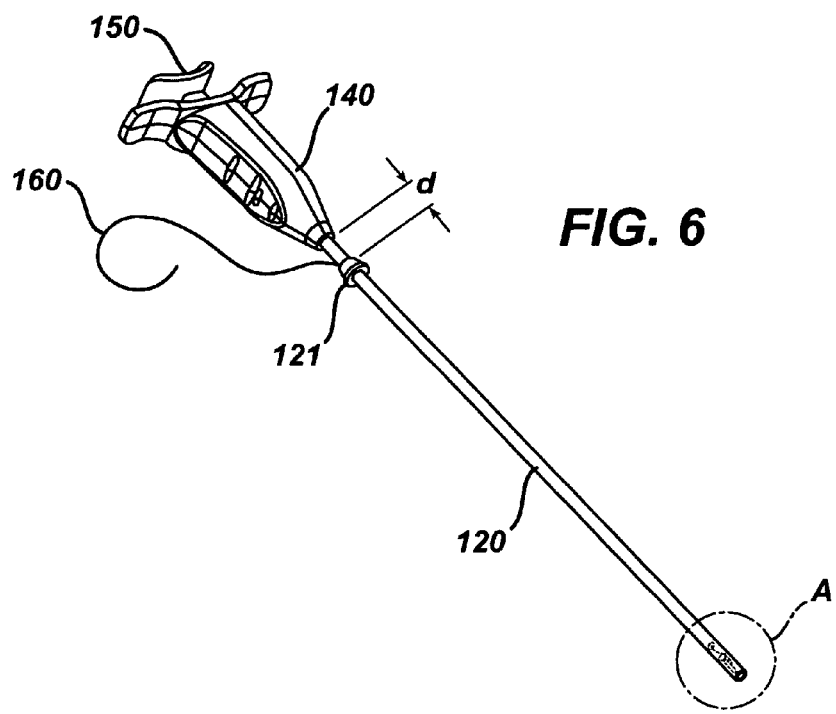
FIG. 6 illustrates illustrates another view, including inset A, of the system of FIG. 5 according to the description herein.
Figure 6A:
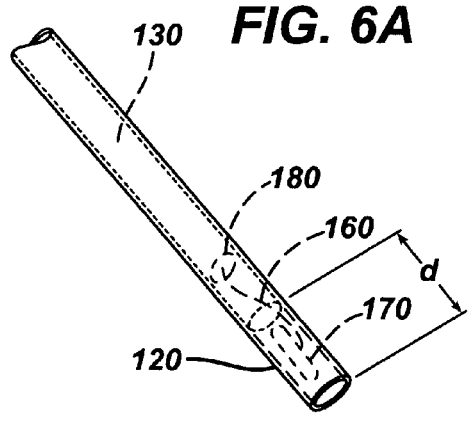
FIGS. 6A and 6B illustrate various views of inset A of FIG. 6 according to the description herein.
Figure 6B:
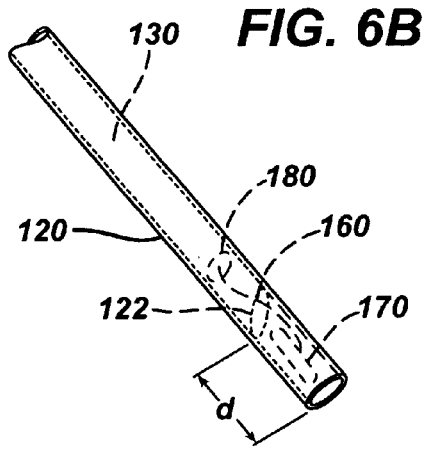
Figure 7:
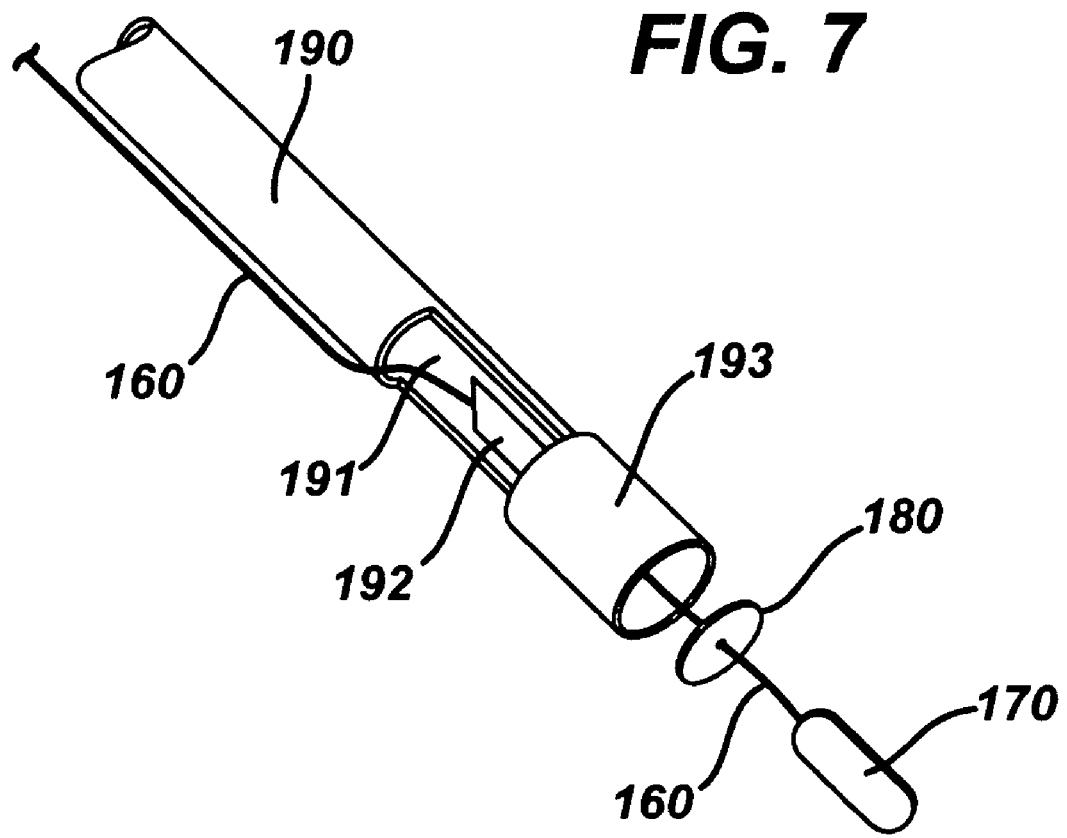
FIG. 7 illustrates aspects of the system of FIG. 5 with the outer sheath and the inner sheath omitted for illustrative purposes according to the description herein.

FIGS. 5-7 illustrate another embodiment of a vessel wound closure system 100 and methods associated therewith. In the embodiment of FIGS. 5-7, the vessel wound closure system 100 comprises an introducer 110 (e.g., from a preceding procedure), an outer sheath 120 slidably disposed through the introducer 110 and having a proximal first position, a distal second position at, or beyond, a distal end of the introducer, and a partially withdrawn third position. The vessel wound closure system of FIGS. 5-7 further comprises an inner sheath 130 (FIG. 6 inset A shown in FIGS. 6A and 6B) slidably disposed within the outer sheath 120 and having a proximal first position and a distal second position at, or beyond, a distal end of the outer sheath in the third position, a handle associated with the outer sheath 120 and the inner sheath 130, a plunger 150 extending through the handle 140 and controlling the disposition of a support rod 190 associated with the plunger 150, a sealing member 170 configured to deploy from a distal end of the outer sheath 120 when the outer sheath 120 is in the third position, an anchor member 180 configured to deploy from a distal end of the inner sheath 130 by depression of the plunger 150, and a suture 160 connecting the sealing member 170 and the anchor member 180, a portion of which suture 160 extends proximal of the anchor member 180 and is accessible to a medical practitioner for manipulation thereof. Deployment of the sealing member 170 within the target vessel generally occurs by inserting the outer sheath 120 through the introducer 110 until a distal end of the outer sheath 120 is positioned at, or beyond, a distal end of the introducer 110 in the target vessel. Partially withdrawing the outer sheath 120 proximally then ideally disposes the sealing member 170 in the target vessel. Movement of the handle 140 distally to locate the inner sheath 130 at its second position such that a distal end of the inner sheath 130 is at, or beyond, a distal end of the outer sheath 120 in the third position helps ensure that the sealing member 170 is successfully deployed within the target vessel. Thereafter, the whole assembly, i.e., system 100, is partially retracted proximally until resistance is felt indicating the sealing member 170 is situated against the inner wall of the target vessel. Then, depressing the plunger 150 and support rod 190 connected thereto disposes the anchor member 180 beyond the distal end of the inner sheath 130, beyond the distal end of the outer sheath 120 and adjacent an outer surface of the target vessel.

The support rod 190 (FIG. 7, wherein the inner sheath 130 and the outer sheath 120 are omitted for illustrative purposes) is preferably connected to the plunger 150, provided within the inner sheath 130, and includes a tamper 193 at its distal end for disposing the anchor member 180 adjacent the outer wall of the target vessel when the plunger 150 is depressed, as discussed above. The support rod 190 further helps to push or maintain the anchor member 180 in place as the anchor member 180 and the sealing member 170 are tightened and secured by the manipulation of the suture 160. The support rod 190 may further comprise a recessed portion 191 and a cutting member 192 for cutting excess suture material after tightening and securing of the sealing member 170 and the anchor member 180 has occurred.

The introducer 110 may further comprise a flared end 111 into which a hub 121 of the outer sheath 120 is received when disposing the outer sheath 120 within the introducer 110. Ideally, receiving the hub 121 of the outer sheath 120 into the flared end 111 of the introducer 110 indicates that a distal end of the outer sheath 120 is positioned at, or beyond, a distal end of the introducer 110, and thus in the target vessel. The outer sheath 120 is then partially withdrawn to deploy the sealing member 170 within the target vessel. The handle 140 is then moved distally to locate a distal end of the inner sheath 130 at, or beyond, a distal end of the outer sheath 120, which helps ensure that the sealing member 170 is deployed within the target vessel. The entire system 100 is then partially retracted until resistance is felt indicating that the sealing member 170 is situated against the inner wall of the target vessel. The plunger 150 is then depressed to expel the anchor member 180 from the distal end of the inner sheath 130 and against the outer wall of the target vessel. The handle 140 may further comprise a removable pull-tab 145 that precludes movement of the handle 140 and inner sheath 130 the additional distance d until removal of the pull-tab 145 has occurred. In this manner, movement of the inner sheath 130 does not occur until the outer sheath 120 has been proximally withdrawn to dispose the sealing member 170 within the target vessel as discussed above. The distal end of the inner sheath 130 may further comprise an angled exit port 122 that helps orient the sealing member 170 or anchor member 180 if desired, to help effect the sealing of the vessel wound upon deployment thereof from the inner sheath 130 and outer sheath 120.

Ideally, the outer sheath 120 thus moves from a first proximal position to a distal second position such that distal end of the outer sheath 120 is located at, or beyond, the distal end of the introducer 110 and in the target vessel when the hub 121 of the outer sheath 120 is within the flared end 111 of the introducer 110. Then, the outer sheath 120 is partially withdrawn proximally to a third position to dispose the sealing member 170 within the target vessel. The handle 140 is then moved distally to locate the inner sheath 130 from a first proximal position to a distal second position such that the distal end of the inner sheath 130 is located at, or beyond, the distal end of the outer sheath 120 in the third position, which helps ensure that the sealing member 170 is deployed within the target vessel as intended. The system 100 is then retracted partially until resistance is felt indicating that the sealing member 170 is situated against the interior wall of the target vessel. The plunger 150, and the support rod 190 connected thereto, are then depressed to expel the anchor member 180 from the distal end of the inner sheath 130 and along an outer surface of the target vessel. The accessible portion of the suture 160 is preferably pulled taught prior to and during depression of the plunger 150 to help maintain the sealing member 170 in place against the interior surface of the target vessel while the anchor member 180 is deployed.

The accessible portion of the suture 160 extends proximal of the anchor member 180 and remains accessible to a medical practitioner to help tighten the sealing member 170 and the anchor member 180 relative to one another after deployment of the sealing member 170 and the anchor member 180 has occurred. Thereafter, the suture 160 is secured to maintain the sealing member 170 and the anchor member 180 about the vessel wound, excess suture material is cut by a cutter 192 (FIG. 7) provided with the support rod 190 within the inner sheath 130, and the unsecured components of the system are removed from the patient.

In practice, an introducer and an assembly is provided, the assembly comprising at least an outer sheath, an inner sheath, a handle, a plunger and a support rod. The sealing member, and the anchor member connected thereto via the suture, are provided in the assembly. The introducer placed through the vessel wound and into the target vessel of a patient. The outer sheath is inserted through the introducer from a proximal first position, to a distal second position, and then partially withdrawn proximally to a third position in order to deploy the sealing member in the target vessel. The handle is then moved distally to locate a distal end of the inner sheath at, or beyond, the distal end of the outer sheath in its third position, which helps ensure that the sealing member is successfully deployed within the target vessel. Thereafter, the assembly of the outer sheath, the inner sheath, the handle, the support rod and the plunger is partially withdrawn until resistance is felt indicating the sealing member is oriented against an interior surface of the target vessel. An accessible portion of the suture may be pulled taught to maintain the sealing member in place against the inner surface of the vessel. The plunger is then depressed to expel the anchor member from the inner sheath and position the anchor member extravascularly along the outer surface of the target vessel. Thereafter, the accessible portion of the suture is manipulated by the medical practitioner to tighten the sealing member and the anchor member relative to one another, and secured, to effect the seal of the vessel wound. Alternatively, the suture could be spring loaded to tighten the sealing member and the anchor member without manual tensioning of the suture. In any event, excess suture material is then cut and unsecured portions of the system are removed from the patient.

Figure 8A:
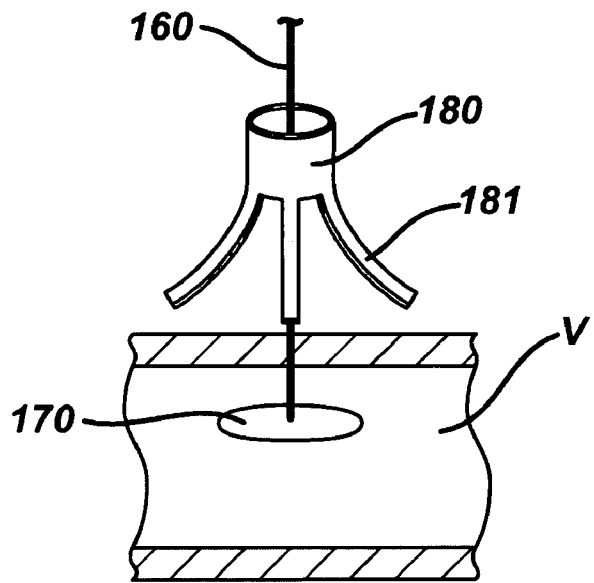
FIGS. 8A and 8B illustrate various other anchor members according to the description herein.
Figure 8B:
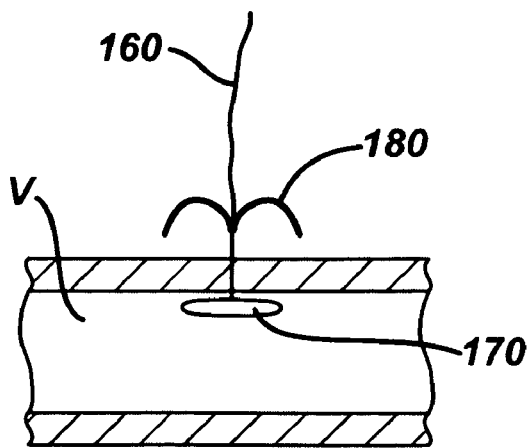

The sealing member 170 and the anchor member 180 may be as described above with respect to FIGS. 3A-3F, or may alternatively be as shown in either of FIG. 8A or 8B, for example. FIG. 8A shows an anchor member 180 having prongs 181 that penetrate into the exterior surface of the target vessel V to secure the anchor member 180 relative to the sealing member 170 after tightening has occurred. FIG. 8B shows an anchor member 180 having an "m" shape that penetrates into the exterior surface of the target vessel V to secure the anchor member 180 relative to the sealing member 170 after tightening has occurred.

The various exemplary embodiments of the invention as described hereinabove do not limit different embodiments of the systems and methods of the invention. The material described herein is not limited to the materials, designs or shapes referenced herein for illustrative purposes only, and may comprise various other materials, designs or shapes suitable for the systems and methods described herein, as should be appreciated by the artisan.

While there has been shown and described what is considered to be preferred embodiments of the invention, it will, of course, be understood that various modifications and changes in form or detail could readily be made without departing from the spirit or scope of the invention. It is therefore intended that the invention be not limited to the exact forms described and illustrated herein, but should be construed to cover all modifications that may fall within the scope of the appended claims.

What is claimed is:

1. A system for closing a wound in a vessel, comprising:
an outer sheath;
a delivery rod slidably disposed within the outer sheath, the delivery rod comprising a first recess, a second recess and an open channel extending between the first recess and the second recess;
a guidewire slidably associated with the delivery rod;
a sealing member arranged in the first recess for deployment thereof from the delivery rod, the sealing member being configured to engage an interior surface of the vessel;
an anchor member arranged in the second recess for deployment thereof from the delivery rod, the anchor member being configured to engage an exterior surface of the vessel; and
a suture connecting the sealing member and the anchor member, the suture arranged in the open channel for deployment thereof from the delivery rod,
wherein the outer sheath and delivery rod are configured such that at a first position the outer sheath prevents the sealing member, the suture, and the anchor member from deploying and at a second position, when the outer sheath and delivery rod have been moved relative to one another, the sealing member, the suture, and the anchor member are deployable,
wherein the delivery rod further comprises an exterior channel and a tapered distal section through which the guidewire slides for locating the system within a target vessel.

2. The vessel wound closure system of claim 1, further comprising a tamping tool, at least a portion of which is disposed within the delivery rod.

3. The vessel wound closure system of claim 2, further comprising a cutting element, at least a portion of which is disposed within the delivery rod.

4. The vessel wound closure system of claim 1, wherein the suture further comprises a connecting portion that connects the sealing member with the anchor member, and an accessible portion that extends proximally of the delivery rod for manipulation thereof by an operator, the connecting portion of the suture being oriented in the open channel of the delivery rod.

5. The vessel wound closure system of claim 4, wherein the anchor member further comprises at least one passageway through which some of the connecting portion of the suture extends.

6. The vessel wound closure system of claim 5, wherein the connecting portion of the suture further comprises one way barbs that pass through the at least one passageway of the anchor member to tighten and secure the anchor member in place relative to the sealing member.

7. The vessel wound closure system of claim 1, wherein the sealing member and the anchor member are comprised of bioresorbable material.

8. The vessel wound closure system of claim 1, wherein the sealing member is larger than the anchor member.

9. The vessel wound closure system of claim 8, wherein the sealing member is elliptical with a width less than an inner diameter of the delivery rod.

10. The vessel wound closure system of claim 8, wherein the sealing member is cylindrical with a diameter less than an inner diameter of the delivery rod.

11. The vessel wound closure system of claim 1, wherein the suture is comprised of bioresorbable material.

\* \* \* \* \*